United States Patent [19]

Omura

[11] Patent Number: 5,720,304

[45] Date of Patent: Feb. 24, 1998

[54] METHOD OF TREATMENT OF SOME RESISTANT INFECTIONS, CANCER AND OTHER DISEASES WHICH HAVE INFECTION AND LOCALIZED METAL DEPOSITS IN PATHOLOGICAL AREAS

[76] Inventor: Yoshiaki Omura, 800 Riverside Dr. (8-I), New York, N.Y. 10032

[21] Appl. No.: 609,530

[22] Filed: Mar. 1, 1996

[51] Int. Cl.[6] .................................. A61B 19/00
[52] U.S. Cl. .......................... 128/898; 47/1.01
[58] Field of Search .................. 47/1.01; 128/898, 128/630

[56] References Cited

U.S. PATENT DOCUMENTS 5,188,107  2/1993  Omura ................................. 128/630

*Primary Examiner*—Vincent Millin
*Assistant Examiner*—Kelly O'Hara
*Attorney, Agent, or Firm*—Kane, Dalsimer, Sullivan, Kurucz, Levy, Eisele and Richard, LLP

[57] ABSTRACT

A method of treatment of *chlamydia trachomatis*, Herpes family viral infections and other medical conditions through the removal of localized heavy metal (eg. Hg) and/or Al deposits and delivering antibiotics and/or antiviral agents along with the ingestion of greens taken from the Umbelliferae family of vegetables including leaves of *Coriandrum Sativum* known as cilantro or Chinese parsley coupled with drug intake enhancement methods.

17 Claims, No Drawings

METHOD OF TREATMENT OF SOME RESISTANT INFECTIONS, CANCER AND OTHER DISEASES WHICH HAVE INFECTION AND LOCALIZED METAL DEPOSITS IN PATHOLOGICAL AREAS

FIELD OF THE INVENTION

The present invention is directed towards a method of treating some resistant infections, cancer and other diseases which have clinical or subclinical infection and localized deposits of heavy metal (e.g. Hg, Pb, Al etc.) in the pathological areas.

BACKGROUND AND SUMMARY OF THE INVENTION

Although it is generally believed and written in many textbooks that *Chlamydia trachomatis* can be eliminated by 1–2 weeks of treatment with effective antibiotics, the treatment of *Chlamydia trachomatis* infection indicated that when antibiotic treatment for localized infection resulted in the disappearance of symptoms, but the infection often recurred, if the treatment was discontinued in less than 1–2 months. It usually took a few months of continuous treatment to completely eliminate recurrence of Chlamydia infection as well as any Bi-Digital O-Ring Test (See U.S. Pat. No. 5,188,107 and file history, the disclosure of which is incorporated herein by reference) resonance response to the monochronal antibody for *Chlamydia trachomatis* in most of the original pathological areas of the body. With non-invasive drug uptake enhancement, the time duration required for disappearance often was reduced to 1 month or less, however often, the infection returned within a few months. Shortly after publication of a study on the problems involved in treatment of *Chlamydia trachomatis*, further examination of the symptom-free subjects following antibiotic treatment, using the Bi-Digital O-Ring Test, detected *Chlamydia trachomatis* response in 3 small, highly specific regions of their bodies, suggesting that *Chlamydia trachomatis* retreats and remains indefinitely in the following 3 parts of the body:

1.) sublingual caruncle (an eminence on each side of the frenulum of the tongue, at the apex of which are the openings of the major sublingual duct and the submandibular duct)

2.) in the right and/or left axillae (at a small round area about nickle size at triangular space formed between the heads of the biceps and triceps muscles)

3.) in the genitals (Corona Glandis area of the Glans Penis, at the Fossa Navicularis of the urethra in the male and near the orifice of the urethra and sometimes in vagina of female)

Some of the areas to which *Chlamydia trachomatis*, Herpes Simplex Types I & II, and Cytomegalovirus often retreat and remain indefinitely in coexistence with Hg, when the original sites of infection are treated with effective antibiotic or antiviral agents. It has recently been found that Insulin-like Growth Factors I & II exist in these areas; however in the presence of infection, significantly reduced amounts of the Insulin-like Growth Factors are found.

Two additional areas to which infectious micro-organisms retreat have recently been located. They are:

1.) The maxillary sinuses, and often ethmoid & frontal sinuses, and small part of nostrils of the face.

2.) The growth line of bones, particularly above and below the knee joints.

Even when drug uptake enhancement of effective antibiotics for *Chlamydia trachomatis* (such as Doxycycline, Erythromycin, and Azithromycin) was used to deliver these medications successfully to the infected areas, the *Chlamydia trachomatis* often persisted for a long period of time becoming a source of recurrent infections. In the process of evaluating the causes of this unexpected lack of effectiveness of the antibiotics, localized Hg deposits were found to be co-existing with and appearing to protect the *Chlamydia trachomatis* from the antibiotic effects of the medication.

In addition, the inventor herein had a cardiac SPECT, with injection of radioactive Thallium 201, which resulted in concentrated deposits of Hg in specific organs such as the heart, liver, kidney, thyroid gland and testes resulting from the rapid decay of Thallium 201 to Hg. Since he had been aware of potential medical problems associated with Hg deposits in the various organs of the human body, he had been using the Bi-Digital O-Ring Test three times a day for estimating Hg deposits non-invasively in different parts of his body, and noting if regularly given strong Shiatsu massage (as drug uptake enhancement method) on the organ representation areas on the hands with or without potential effective substances would enhance the excretion of mercury.

The inventor fortuitously ate 2 cups of Saigon Soup which contained a relatively large amount of Chinese parsley, (also known as cilantro) from a Vietnamese restaurant for dinner, Less than 10 hours later, upon testing, a marked reduction of Hg in various organs of the body was found. Subsequent measurement, before and after taking Chinese parsley, indicated significant increase in urinary secretion of Hg, Pb, and Al, and a decrease in deposited Hg in the different organs. Enhanced urinary excretion of Cd and Ni was also found. Cilantro, or Chinese parsley was then eaten 3–4 times/day (5–10 grams of raw leaves each time) resulting in further Hg reduction. The inventor has also compared effects of different types of parsleys and leaves of related plants on himself as well as on many volunteers.

Chinese parsley (leaf of *Coriandrum Sativum*, also known as Cilantro) is a member of the Umbelliferae family of vegetables which includes leaves of various types of parsley (such as curly leaved parsley, flat leaved parsley, Mitsuba, etc.) and green leaves of caraway, carrots, celery, dill, fennel, and parsnips. The inventor discovered that when taken in sufficient amounts, the green leaves of these vegetables have the capability of eliminating localized Hg deposits from the body tissues in varying degrees. Chinese parsley was found to be the most effective, and carrot greens (the leaves) appear to be next in effectiveness & safety. While both curly and flat-leaved parsley had some effect in promoting urinary excretion of Hg, they were not found to be as efficient and safe as the Chinese parsley and carrot greens. Both flat and curly parsley have toxic effects on the liver, heart and brain when taken in excessive amounts with much narrower therapeutic window than Chinese parsley, according to the Bi-Digital O-Ring Test. The dried seed of Chinese parsley is known as coriander, but it was found that it had little Hg reduction effect as the therapeutic window is very narrow. The variety of herbal plants known as parsley includes: 1) French (American) or curly parsley (*petroselinum crispum*), 2) Italian or Genovese parsley, 3) Hamburg parsley (*petroselinum crispum* or *tuberosum*), 4) Japanese parsley, "Mitsuba", (*Cryptotaenia canadensis*, Uaponical), 5) Chervil or Beaked parsley (*Anthriscus cerefolium*), 5) Chinese parsley or Mexican parsley (cilantro). According to the folk medicine legend, parsley stimulates uterine muscle contraction and it is also known as a folk medicine to induce labor or abortion, and therefore should not be taken by pregnant women. It also has a diuretic effect and should therefore be taken with sufficient fluid or water.

Chinese parsley had the best result compared with all the related plants in both removing Hg and safety range (broader therapeutic window). These vegetable/herbs were then used by the inventor with the subjects who were still taking antibiotics with drug uptake enhancement in the attempt to eradicate the *Chlamydia trachomatis* which still remained in the aforenoted 'hiding places'. This combined treatment reduced the infection significantly, but still did not completely eliminate the *Chlamydia trachomatis* from at least 3 of the 5 areas to which it had apparently retreated.

It is a principal object of the invention to provide an effective method of treatment of *chlamydia trachomatis*, Herpes family viral infections and other medical conditions.

It is a further object to effect such treatment through the removal of localized heavy metal (eg. Hg) deposits and delivering effective antibiotics and/or antiviral agents.

It is a further object to provide a method of treatment when the localize Hg deposits are removed through the ingestion of greens taken from the Umbelliferae family of vegetables including cilantro (leaves of *coriandrum sativum*) coupled with drug intake enhancement methods.

The present invention provides for a method of treating a wide range of ailments through the use of greens taken from the Umbelliferae family of vegetables, antibiotics, antiviral agents and drug uptake enhancement techniques. This includes eating actual Chinese parsley or drinking Chinese parsley juice, in a sufficient amount, or taking Chinese parsley tablets prepared by The Hayashibara Biochemical Research Laboratory of Okayama City, Japan by the inventor's request. This latter method is an easily absorbable form of Chinese parsley in controlled amounts (by mg). It was found to eliminate more effectively the localized Hg deposits which appeared to be protecting the microbial infections from the antibiotics, or to be rendering the antibiotics ineffective. When drug uptake enhancement procedures were used regularly to assure delivery of the effective antibiotic and Chinese parsley's effective component to the affected area(s) continuously and localized deposits of Hg, Pb or other metals were eliminated, the last traces of Chlamydia were eliminated completely, or the process of eliminating them was accelerated.

It is believed the effective or major component comprises Bergapten, Umbelliferone, Scopoletin, Xanthotoxol with or without imperatorin, Beta-sitosterol, and Alpha-Amyrin alone or in combination with the others. (See Publication, Constitute of *Coriandrum Sativum* and *Pituranthos Triradiatus*, Bulletin of Faculty of Pharm, Cairo University, 1993. Volume 31, Number 3.) Concerning Chinese parsley's effective or major component, I found the following: alcohol can extract the effective component very effectively. For example, even 10–15% alcohol containing wine like various Japanese plum wines or grape wine (such as Manischewitz Kosher wine) can extract effective component from immersed Chinese parsley leaf in one minute and remaining Chinese parsley leaf has no effective component. By boiling Chinese parsley leaf in water, no effective component is extracted, but effective component remains inside of the boiled leaves. Therefore at least, the effective component is resistant to heat of at least 100 degrees Centrigrade. Since the effective component is not destroyed by temperature between 100–110 degrees Centigrade, one dose of Chinese parsley can be prepared by either a freeze dry method or heat-drying of the homogenate of 5–8 grams of fresh leaves of Chinese parsley, which reduces the weight to about one-tenth and can be put in the empty geg capsules, or it can be made highly absorbable form such as mixing with a sugar base and compressed as a dry tablet of known amount as made by the aforementioned company.

The method was also successfully used in eliminating Herpes Simplex Type I & Type 2, and Cytomegalovirus infection in various parts of the body, as Hg deposits usually coexist in the Herpes family virus infected areas as well. One of the most common causes of intractable pain is produced by Herpes Simplex Viruses, Type I or Type II. Headache is commonly caused by Herpes Simplex Virus, Type I, which often produces blood vessel infection in the cerebral cortex of the brain. These viral infections also often coexist with localized deposits of Pb, with or without Hg, in the motor cortex on the abnormal side of the brain of stroke patients. Clinical experiences of the treatment of subjects with intractable *Chlamydia trachomatis* infection and/or Herpes Family Viral infections will be discussed.

In addition, the effect of using a combination of two food supplements, EPA with DHA as an antiviral agent, and Chinese parsley tablets to remove the localized Hg deposits from the cancer cell nuclei, in a number of patients with various types of cancer. With use of some of the various drug uptake enhancement methods previously described, this treatment has shown very promising results.

DETAILED DISCUSSION OF THE PREFERRED METHOD

Thirteen subjects participated in a preliminary study on the treatment of various intractable infections, but two were not included herein since they became unavailable for follow-up. (This study, the results and conclusion can be found in an article to be published in Accupuncture and Electro-Therapeutics Research, The International Journal Vol. 20, Numbers 3 and 4 (delayed combined edition) entitled "Role of Mercury (Hg) in Resistant Infections & Effective Treatment of *Chlamydia Trachomatis* and Herpes Family Viral Infections (and Potential Treatment for Cancer) by Removing Localized Hg Deposits with Chinese Parsley and Delivering Effective Antibiotics Using Various Drug Uptake Enhancement Methods".) The eleven subjects who remained in this study were as follows:

1) Six individuals with *Chlamydia trachomatis:* 5 females (a 26 y.o. Eurasian-American female, a 30 y.o. Asian-Brazilian female, a 57 y.o. white American female, a 59 y.o. Asian-American female, and a 60 y.o white American female), and one 40 year old white American male.

2) Four individuals with Herpes Simplex Types I & II Viruses: 2 white American females, ages 40 and 45; and 2 males: a 28 y.o. white American and a 61 y.o. Asian-American.

3) One individual with Cytomegalovirus: a 61 year old Asian-American male.

Most of the subjects had persistent symptoms, had been treated by physicians who had attempted diagnoses without success, and/or had been treated symptomatically without relief. The presenting symptoms included joint pain in the knees, fingers, wrists, shoulders, and feet, back pain, itching, migraine headache, mild aphasia, confusion, hypoglycemia, diarrhea, abdominal discomfort, sore throat, toothache, flu-like symptoms with fatigue and muscle aches, and facial discomfort.

The subjects were evaluated with the Bi-Digital O-Ring Test for infections and their pertinent biochemical parameters. Those with *Chlamydia trachomatis* were given Doxycyclene, 100 mg, 2 times/day, with Chinese parsley, a dietary supplement given 3–4 times/day to clear coexisting localized Hg deposits. Since the exact amounts of cilantro, Chinese parsley, or parsley being absorbed were unknown, a Chinese parsley tablet containing controlled amounts were made in a sugar base. Only the first subject received 25 mg doses of the Chinese parsley tablets 4 times/day; subsequent subjects took between 75 and 100 mgs, 3–4 times daily.

The search continued for optimal drug uptake enhancement methods. Red spectra from a light-emitting diode, red monochromatic Laser beam, and white light exposure from both a DC battery flashlight and an AC lamp light bulb, as well as fluorescent light, were compared for their effects on localized drug uptake. The inventor found that an inexpensive red broad-spectra light emitting diode was as effective for drug uptake enhancement as a Laser beam of comparable output, but that fluorescent light inhibited drug uptake. While the red light from a pen light with a red filter increased uptake in the specific organ represented by its hand representation area, the red light from regular flashlight or brighter Krypton flashlight with red filter significantly enhanced drug uptake not only in the specific organ, but also in the surrounding area, a preferable condition. However, light beam from Halogen or Xenon high intensity flashlight inhibited drug uptake and prolonged exposure may be potentially harmful.

Drug uptake enhancement was provided by one of the following methods selected from a comprehensive following listing of procedures:

1.) Vigorous Shiatsu massage of organ representation areas on the hand for a minimum of 1–2 minutes 4 times/day.

2.) (+)Qi Gong energy stored paper placed directly on the organ representation areas 4 times/day.

3.) (+)Qi Gong energy stored paper placed on the cardiovascular representation area of the Medulla Oblongata on the occipital area of the scalp 4 times/day.

4.) (+)Qi Gong energy stored paper placed on the affected areas on various parts of the body 4 times/day.

5.) Light from a standard tungsten bulb or, preferably, a brighter Krypton bulb battery operated flashlight with red filter, or broad-spectra from a light emitting diode applied, or monochronal red Laser light for a minimum of 1–2 minutes on the organ representation areas on the hands (or ears or feet) 4 times/day or directly above the pathological areas.

6.) Negative electrical field application to the organ representation areas 4 times/day from a series of 2–5 connected 9-volt batteries (total 18–45 V), or above pathological area, if applicable.

7.) Piezo electric pulses on the organ representation areas, or on the pathological areas, if applicable.

8.) South pole of magnetic field (800–3000 gauss) applied for 1–2 minutes on the organ representation areas of the body, 4 times/day.

9.) Acupuncture given 1–2 times/week to the appropriate point or area where there is no infection.

Since late 1993 the inventor has been successfully estimating blood and tissue concentrations of various substances, including blood glucose, Uric acid, and cholesterol, non-invasively, using the Bi-Digital O-Ring Test. The inventor discovered that when using known amounts of different substances as reference controls (substances compared for resonance), a striking maximum O-Ring weakening resonance phenomenon occurs between the control and the test substances when the 2 substances are identical and of equal amounts. Based on this principle, the inventor was able to determine whether or not abnormality exists in a specific location, and if so, whether it is a viral, bacterial, or some other type of infection, a toxic substance, or a micro-circulatory disturbance. Through the use of the reference control substances and resonance phenomenon between 2 identical substances, one is also able to determine the presence or absence of Thromboxane $B_2$ and Acetylcholine, the potential effectiveness or ineffectiveness of various medications, and the degree of drug uptake in the pathological parts of the body when medications are taken. Estimation of venous blood chemistry is done non-invasively using the Bi-Digital O-Ring Test at the surface of the largest vein in the hand or forearm in areas where bone tissue does not exist below the vein. The grading of the resonance response between 2 identical substances is expressed as maximum=+6 (O-Ring opens completely) and minimum=0 (when the O-Ring does not open at all). As discussed in U.S. Pat. No. 5,188,107 the Bi-Digital O-Ring Test has both a direct and an indirect method, in the direct method testing is performed by the examiner using the patient's hand, while in the indirect method the examiner uses the fingers of an intermediary. In order to use the Bi-Digital O-Ring test in either method, the following 3 essential conditions must be satisfied:

1st Condition: A Bi-Digital O-Ring must be formed (by the thumb and one other finger of the examinee) that cannot be opened by the examiner's interlinked Bi-Digital O-Rings, (made by his/her thumbs and index fingers) pulling from both sides of the examinee's O-Ring.

2nd Condition: The Bi-Digital O-Ring selected in the 1st Condition must open to near maximum extent [or at least ¾ (–3) of the maximum opening (4)] when the examiner adds the middle fingers of both hands to his interlocking rings and pulls.

3rd Condition: The patient's or intermediary's O-Ring that satisfies the first 2 conditions must again satisfy the 1st condition while his/her head is held in 4 different positions: chin down, chin up, facing right, facing left.

When the examinee's O-Ring formed between thumb and a selected one of the remaining 4 fingers satisfies the above 3 essential conditions, it is designated as the Control (Bi-Digital) O-Ring. When only the Control O-Ring opens, notation may be recorded using a single upward pointing arrow or (+1). If the Control O-Ring and the next stronger one both open, it is noted as 2 upward arrows, or (+2), etc. When the examinee's possible O-Rings are used up, the examiner makes his interlocking rings weaker, step by step, by substituting progressively weaker digits for the index finger-thumb combination. Each of the examiner's weakening steps is noted as an additional upward arrow or +, making the strongest possible response a notation of 6 arrows or (+6) since our Control O-Ring was between the thumb and 4th finger, (provided that repeated tests are done by the same examiner and examinee).

The majority of the subjects examined had blood chemistry evaluation by standard laboratory testing and comparison of the reports with the results of the non-invasive Bi-Digital O-Ring Test. Estimation of Uric acid and other substances in different organs was performed on the skin surface directly above that organ using premeasured amounts of Uric acid or other chemicals (including various neurotransmitters) as control substances. These materials were enclosed in 0.7 cc plastic micro-test tubes (#3813) with hanging caps made by the Eppendorf Company in Germany, or 0.5 cc micro-centrifuge tubes (8×30 mm, catalog #110560) made by Globe Scientific, Inc., Paramus, N.J. Most of the chemicals used in this study were obtained from Sigma Chemical Company, St. Louis, Mo. To identify *Chlamydia trachomatis*, Herpes Simplex Type I, Herpes Simplex Type II, Cytomegalovirus, and other viruses, their monoclonal antibodies were used as reference control substances. To identify the presence of heavy metals (Pb and Hg) known amounts were used as reference control substances. Unlike the measurement of organic substances by the Bi-Digital O-Ring Test in which resonance is maximal between identical amounts of identical substances, the measurement of heavy metals requires reference control substances of more than 10 times the amount in the tissues or urine. However, since these amounts are roughly proportional to the quantities existing in the body tissue or fluids, the measurements are of value in estimating the presence of these metals and their changes in magnitude.

(+)Qi Gong energy was stored on 3"×5" index cards or note paper. The drug uptake enhancement methods were applied to the organ representation areas of different parts of the body. Most commonly, the accurate organ representation areas of the hands and other parts of the body (ear, head, tongue, feet) is mapped using the Bi-Digital O-Ring test resonance phenomenon between two identical substances as described earlier.

Accurate organ representation areas are mapped using the Bi-Digital O-Ring test because the organ representation area maps of the hands used by the North Korean and South Korean schools of acupuncture are inaccurate. Accurate and detailed organ representation area mapping of the feet can also be done. It should be noted that organ representation area maps of the feet widely used by others in the past are at least 50% inaccurate, and therefore, without mapping of the accurate organ representation areas on the hands and feet, it would have been difficult to obtain accurate results.

Clinical experiences of the treatment of subjects with intractable *Chlamydia trachomatis* infection and/or Herpes Family Viral infections are presented below. The method described here is also currently being applied with a group of cancer patients in whom cancer has been confirmed by histological studies, with the initial results promising.

Clinical Case 1:

The process of eliminating *Chlamydia trachomatis* infection was extensively documented in the first subject, a 60 year old white American female speech/language pathologist, in whom the inventor succeeded in eliminating the infection in the last 3 localized areas to which this inventor had hypothesized the Chlamydia retreats to avoid the antibiotic. (Later 2 more such locations were identified).

*Chlamydia trachomatis* remained impervious to antibiotics in these sites even when drug uptake enhancement methods were used to direct antibiotics to these 3 specific locations. Since this inventor's previous study indicated that the presence of Hg deposits in those locations was inhibiting antibiotic effects, estimation for the relative amount of Hg deposited in localized tissue was performed using the Bi-Digital O-Ring Test. Maximum resonance was found between the pure mercury sample of 11 mg* and the Hg existing at the sublingual caruncle, the axillae, and the genitals which was <1.1 mg of Hg in the tissues. Uric acid was also elevated in these areas, averaging about 11 mg/dl, while blood Uric acid level was within normal levels (6.0 mg/dl).

* The number of mg of Hg reported on the charts refers to the amount used as the reference control substance, not to the actual estimated amount in the tissues. Normally the Bi-Digital O-Ring Test resonance phenomenon becomes maximum between 2 identical substances (one being the reference control substance) when the amounts of these 2 substances are also identical. In the case of organic molecules, such as uric acid or glucose, the amount of the pure identical substance used as a reference control substance to obtain maximum resonance is very close to the amount of the same molecules to be examined in body tissues or fluids. A very distinctive sharp peaked resonance results, which is therefore clinically very valuable as a simple, quick, and economical non-invasive quantitative measurement method for organic molecules. However there is an exception in the case of metals. The amounts of pure heavy metals required as reference control substances to create maximum resonance is more than 10 times greater than the amount of identical heavy metal in the tissues or urine. The pattern of the resonance with heavy metal is not as narrow a peak as with two identical organic molecules; rather, it is very broad. In reporting the measurement of mercury, we have used the indication, "Hg*" because 11 mg of Hg corresponds to less than 1.1 mg./dl in body tissue concentration. However, it is a useful measure as the amount of the reference control substance required to produce resonance is roughly proportional to the amount existing in the tissues or urine.

| Time | Area | Chlamydia | Hg* | Uric Acid |
| --- | --- | --- | --- | --- |
| Pretreatment | **Sublingual C. | +6 (max) | 11 mg | 11 mg/dl |
| 9/2/95 | Axillae | +6 (max) | 11 mg | 11 mg/dl |
| (Sat. 7 pm) | Genitals | +6 (max) | 11 mg | 11 mg/dl |

**Sublingual C. is an abbreviation for sublingual caruncle

Chinese parsley (cilantro), and parsley were demonstrated to promote very significant excretion of Hg, Pb, or Al deposits from infected areas of the body. Therefore during a course of 60 hours, Doxycycline, 100 mg, and dried Chinese parsley, about 2-3 grams in a cup of water, were taken twice daily. Shiatsu massage was applied to the representation areas for the sublingual caruncle, axillae, and vagina on the hands each time medication was taken. Testing of *Chlamydia trachomatis*, Hg, and Uric acid response with the Bi-Digital O-Ring Test revealed the following:

| Time | Area | Chlamydia | Cytomegalovirus | Hg* | Uric acid |
| --- | --- | --- | --- | --- | --- |
| After 51 hours | Sublingual C. | +2 | +6 | 3 mg | 5 mg/dl |
| 9/5/95 | Throat | | +2 | | |
| (Tues. 10 pm) | Axillae | +1 | +6 | 1 mg | 5 mg/dl |
| | Genitals | +2 | +6 | 1 mg | 5 mg/dl |
| After 97 hours | Forehead | | +2 bilaterally | | |
| 9/7/9 | Hippocampus | | +3 | | |
| (Thurs. 8 pm) | Sublingual C. | +1 | +6 | 1 mg | 5 mg/dl |
| | Throat | | +6 | | |
| | L. axilla | +1 | +2 | 1 mg | 5 mg/dl |
| | R. axilla | +2 | +2 | 2 mg | 6.5 mg/dl |
| | Genitals | +2 | +6 | 1 mg | 5 mg/dl |
| After 7 days | Forehead | | +6 bilaterally | | |
| 9/10/95 | Hippocampus | | +3 bilaterally | | |
| (Sun. 7 pm) | Sublingual C. | +1 | +2 | 1 mg | 5 mg/dl |
| | Throat | | +6 | | |

-continued

| Time | Area | Chlamydia | Cytomegalovirus | Hg* | Uric acid |
|------|------|-----------|-----------------|-----|-----------|
|  | L. axilla | +2 | +2 | 1 mg | 5 mg/dl |
|  | R. axilla | +2 | +2 | 2 mg | 6.5 mg/dl |
|  | Genitals | +2 | +2 | 1 mg | 5 mg/dl |

At this point the subject was exposed to many clients who had upper respiratory flu-like symptoms. She developed a sore throat followed by a sensation of heaviness in her head together with general malaise. The Bi-Digital O-Ring Test revealed Cytomegalovirus in the throat, and in the areas still infected with Chlamydia. EPA, 180 mg, with DHA 120 mg, was indicated to be much more effective than the well known antiviral agent, Acyclovia, and was therefore taken 4 times/day. There was no negative drug interaction or canceling effect with the Doxycycline.

| Time | Area | Chlamydia | Hg* | Uric acid |
|------|------|-----------|-----|-----------|
| After 24 hours | Sublingual C. | +5 | 10 mg | 10 mg/dl |
| 9/4/95 | Axillae | +5 | 10 mg | 10 mg/dl |
| (Mon. 7 pm) | Genitals | +6 | 11 mg | 11 mg/dl |
| After 26 hours | Sublingual C. | +4 | 9 mg | 9 mg/dl |
| (Mon. 9 pm) | Axillae | +4 | 7 mg | 7 mg/dl |
|  | Genitals | +6 | 11 mg | 11 mg/dl |
| After 30 hours | Sublingual C. | +3 | 6 mg | 6 mg/dl |
| 9/5/95 | Axillae | +3 | 6 mg | 6 mg/dl |
| (Tues. 1 am) | Genitals | +6 | 10 mg | 10 mg/dl |
| After 39 hours | Sublingual C. | +2 | 3 mg | 5 mg/dl |
| (Tues. 10 am) | Axillae | +2 | 3 mg | 5 mg/dl |
|  | Genitals | +4 | 6 mg | 7 mg/dl |

On Saturday, Sep. 16, 1995, at 8 pm the treatment protocol was again changed. In addition to Doxycycline 100 mg, 2 times/day, and EPA, 180 mg with DHA, 120 mg, 4 times/day, Chinese parsley tablets, 25 mg, 4 times/day were added to replace the dried Chinese parsley used previously. Within 12 hours, on Sep. 17, 1995, after the 1st Chinese parsley tablet was taken, Chlamydia was tested and found to be +0 in the areas listed below. Two days later, testing revealed the following findings:

| Time | Area | Chlamydia | Cytomegalovirus | Hg* | Uric acid |
|------|------|-----------|-----------------|-----|-----------|
| After 16 days | Head |  | +0 |  |  |
| 9/19/95 | Sublingual C. | +0 | +2 | 6 mg | 5 mg/dl |
| (Tues. 7 pm) | L. axilla | +0 | +0 | 6 mg | 5 mg/dl |
|  | R. axilla | +0 | +0 | 6 mg | 5 mg/dl |
|  | Genitals | +0 | +0 | 6 mg | 5 mg/dl |

However, when this inventor tested *Chlamydia trachomatis* at the areas infected by Cytomegalovirus, he found the following:

| Area | Chlamydia | Cytomegalovirus | Hg* | Uric acid |
|------|-----------|-----------------|-----|-----------|
| Nostrils | +6 | +6 | 11 mg | 10 mg/dl |
| L. ear | +6 | +6 | 11 mg | 10 mg/dl |
| R. ear | +6 | +6 | 11 mg | 10 mg/dl |

Medication was continued, but the subject inadvertently forgot to stimulate the organ representation areas for the ears for selective drug uptake enhancement. By the next day, Hg deposits and Uric acid had increased in the ear canals:

| Time | Area | Chlamydia | Cytomegalovirus | Hg* | Uric acid |
|------|------|-----------|-----------------|-----|-----------|
| 9/20/95 | Head |  | +0 | 0.5 mg | 5 mg/dl |
| (Wed. 9 am) | L. axilla | +0 | +0 | 0.5 mg | 5 mg/dl |
|  | R. axilla | +0 | +0 | 0.5 mg | 5 mg/dl |
|  | Genitals | +0 | +0 | 0.5 mg | 5 mg/dl |
|  | Nostrils | +6 | +6 | 0.5 mg | 5 mg/dl |
|  | L. Ear | +6 | +6 | 20 mg | 15 mg/dl |
|  | R. Ear | +6 | +6 | 20 mg | 15 mg/dl |
| (after 20 hours) | Sublingual C. | +0 | +0 | +0 mg | 5 mg/dl |
| 9/23/95 | Throat |  | +6 |  |  |
| (Sat. midnight) | L. axilla | +1 | +0 | +2 mg | 5 mg/dl |
|  | R. axilla | +1 |  | +2 mg | 6.5 mg/dl |
|  | Genitals | +2 |  | +3 mg | 5 mg/dl |
|  | Nostrils | +3 |  | +4 mg | 10 mg/dl |
|  | L. ear | +3 |  | +4 mg | 10 mg/dl |
|  | R. ear | +3 |  | +4 mg | 10 mg/dl |
|  | Forehead | +3 | +6 |  |  |

The inventor had previously studied the effects of light spectra of different wave lengths on drug uptake when the light is directed to the cardiovascular representation area of the Medulla Oblongata on the occipital area of the scalp. This study indicated that wave lengths of the colors green, blue, and purple, fluorescent light, and ultraviolet light inhibit drug uptake to pathological areas. It also demonstrated that when an infected organ or its representation area is exposed to red light or near infrared spectrum light, drug uptake is selectively enhanced in that organ.

To ascertain the most effective drug uptake enhancement method, I decided to compare the differences between red spectra from a light-emitting diode, red monochromatic Laser beam, and white light from both a DC battery flashlight (including regular flashlight, 70% brighter Krypton bulb flashlight & 300% brighter Halogen bulb flashlight) with or without red filter and an AC lamp light bulb. The ulnar side of the top half of the distal phalange of the middle finger of the right hand was exposed to each light source for 10 seconds. Between exposures drug uptake was canceled completely by exposing the area to a 4 Watt fluorescent light for about 5 seconds. The inexpensive red broad-spectra light emitting diode is often effective for drug uptake enhancement than that of the Laser beam of comparable output. While the red light from a pen light or regular flashlight with a red filter increased drug uptake in the specific organ (the right side of the head) represented by that hand representation area more effectively than without red filter. Use of the light from a small flashlight and 70% brighter Krypton bulb flashlight with red filter was added for drug uptake enhancement to the treatment 12 hours later, further experimentation revealed that while the light with or without red filter caused both the Doxycycline and the EPA/DHA to be delivered to the infected areas, (+) Qi Gong energy stored paper applied to the Medulla Oblongam representation area at occipital area exerted a more selective effect favoring uptake of the Doxycycline. The Qi Gong, an organic energy, appears to have some form of biological intelligence instructing it to sequence the bombardment of the two infections in the body according to its choice of priority.

| Time | Area | Chlamydia | Cytomegalovirus | Hg* | Uric acid |
|---|---|---|---|---|---|
| 9/24/95 | Sublingual C. | +0 | | +0 mg. | 5 mg/dl |
| (Sunday noon) | L. axilla | +1 | | +1 mg. | 5 mg/dl |
| | R. axilla | +1 | | +1 mg. | 5 mg/dl |
| | Genitals | +2 | | +3 mg | 6 mg/dl |
| | Nostrils | +1 | +1 | +1 mg | 5 mg/dl |
| | L. ear | +1 | | +1 mg | 5 mg/dl |
| | R. ear | +1 | | +1 mg | 5 mg/dl |
| | Forehead | +1 | +0 | +3 mg | 5 mg/dl |
| | Occiput | +½ | +0 | +1 mg | 5 mg/dl |
| | Throat | | +6 | | |

Drug uptake enhancement was changed to intensified (+)Qi Gong energy stored paper applied to the Medulla Oblongata for about 1 minute at least twice a day. Testing about 11 hours later revealed these changes:

| Time | Area | Chlamydia | Cytomegalovirus | Hg* | Uric acid |
|---|---|---|---|---|---|
| 11:00 pm | Sublingual C. | +1 | | +0 mg. | 5 mg/dl |
| 9/24/95 | L. axilla | +0 | | +0 mg. | 5 mg/dl |
| | R. axilla | +0 | | +0 mg | 5 mg/dl |
| | Genitals | +2 | | +3 mg | 6 mg/dl |
| | Nostrils | +1 | | +0 mg | 5 mg/dl |
| | L. ear | +1 | | +0 mg | 5 mg/dl |
| | R. ear | +1 | | +0 mg | 5 mg/dl |
| | Forehead | +0 | +6 | +11 mg | |
| 11:00 am | Sublingual C. | +0 | | +0 mg. | 5 mg/dl |
| 9/25/95 | L. axilla | +0 | | +0 mg. | 5 mg/dl |
| | R. axilla | +0 | | +0 mg | 5 mg/dl |
| | Genitals | +2 | | +3 mg | 6 mg/dl |
| | Nostrils | +0 | | +0 mg | 5 mg/dl |
| | L. ear | +0 | | +0 mg | 5 mg/dl |
| | R. ear | +0 | | +0 mg | 5 mg/dl |
| | Forehead | +0 | | | |
| | Occiput | | +6 | +11 mg | |
| | Esophagus (sphincter) | | +6 | +11 mg | |

By the evening the Cytomegalovirus was eradicated and only weak response to Chlamydia trachomatis was found in the genital area.

| Time | Area | Chlamydia | Cytomegalovirus | Hg* | Uric acid |
|---|---|---|---|---|---|
| 6:30 pm | Sublingual C. | +0 | | +0 mg | 5 mg/dl |
| 9/25/95 | L. axilla | +0 | | +0 mg | 5 mg/dl |
| | R. axilla | +0 | | +0 mg | 5 mg/dl |
| | Genitals | +1 | | +0.5 mg | 5 mg/dl |
| | Nostrils | +0 | | +0 mg | 5 mg/dl |
| | L. ear | +0 | | +0 mg | 5 mg/dl |
| | R. ear | +0 | | +0 mg | 5 mg/dl |
| | Forehead | +0 | | | |
| | Occiput | | +0 | | |
| | Esophagus (sphincter) | | +0 | +0 mg | |

Five days later, however, the subject complained of joint pain in the large toes on both feet. Testing with the Bi-Digital O-Ring Test revealed:

| Time | Area | Chlamydia | Cytomegalovirus | Hg* |
|---|---|---|---|---|
| 5:00 pm | Sublingual C. | +0 | | +0 mg |
| 9/30/95 | L. axilla | +0 | | +0 mg |
| | R. axilla | +0 | | +0 mg |
| | Genitals | +0 | | +0 mg |
| | Nostrils | +0 | | +0 mg |
| | L. ear | +0 | | +0 mg |
| | R. ear | +0 | | +0 mg |
| | Forehead | +0 | | |
| | Occiput | | +0 | |
| | Esophagus (sphincter) | | +0 | +0 mg |
| | R. big toe | +6 | | +11 mg |
| | L. big toe | +6 | | +11 mg |

Doxycycline was continued and the dosage of the Chinese parsley tablets doubled to 50 mg, 4 times/day. Drug uptake enhancement was accomplished with vigorous Shiatsu massage of the whole thumb and small finger on both hands 4 times daily. Twenty-nine hours later there was no response to Chlamydia trachomatis and only small traces of Hg remained in the large toes.

| Time | Area | Chlamydia | Cytomegalovirus | Hg* |
|---|---|---|---|---|
| 10:00 pm | Sublingual C. | +0 | | +0 mg |
| 10/1/95 | L. axilla | +0 | | +0 mg |
| | R. axilla | +0 | | +0 mg |
| | genitals | +0 | | +0 mg |
| | nostrils | +0 | | +0 mg |
| | L. ear | +0 | | +0 mg |
| | R. ear | +0 | | +0 mg |
| | Forehead | +0 | | |
| | Occiput | +0 | | |
| | Esophagus (sphincter) | | | +0 mg |
| | R. big toe | +0 | | +0.5 mg |
| | L. big toe | +0 | | +0.5 mg |

Two days later, on Oct. 3, 1995 at 9:00 pm, testing revealed that Chlamydia was gone from all sites and the last traces of Hg at the bases of the large toes had disappeared. Antibiotic and Chinese parsley tablets were discontinued the next day with no recurrence of the infections.

Clinical Case 2

A 26 year old Eurasian-American female, working in the television industry, had Chlamydia trachomatis infection diagnosed with the Bi-Digital O-Ring Test 6 years ago, while attending college. The infection was treated repeatedly with Erythromycin for at least 1 month each time. There was always a disappearance of the symptoms, but recurrence of the infection a few months later. Her symptoms included frequent gastrointestinal discomfort and lightheadedness unless she ate frequent small meals during the day. Her physician repeatedly tested for hypoglycemia with two hour glucose tolerance tests but glucose levels always tested within normal limits. Four hour glucose tolerance tests were not done. When she came to the inventor for examination, the Bi-Digital O-Ring Test indicated *Chlamydia trachomatis* infection in the genito-urinary system, and in the pancreas *Chlamydia trachomatis* with Cytomegalovirus. Frequent non-invasive measurements of blood glucose levels done with the Bi-Digital O-Ring Test indicated recurrent fluctuating levels, from about 10 minutes of normal level (about 60–100 mg/dl) to 1–2 minute periods of hypoglycemic levels (about 40 mg/dl).

Erythromycin was given with (+)Qi Gong energy stored paper applied to the occipital area over the cardiovascular representation area of the Medulla Oblongata for drug uptake enhancement to treat the *Chlamydia trachomatis* which was judged to be the dominant infection. Unfortunately EPA/DHA, the most effective agent found by the Bi-Digital O-Ring Test against Cytomegalovirus, has a canceling inter-action with Erythromycin. Therefore treatment of the Cytomegalovirus was done by timing the dosages carefully, leaving about 2 hours between taking the drug for *Chlamydia trachomatis* and the antiviral agent for CMV. This treatment eliminated the infection in the genito-urinary system and markedly reduced the symptoms and infection in the pancreas, but within 3 months of discontinuing the treatment, symptoms and infections would recur. A one week treatment of Azithromycin was followed and extended for an additional week which resulted in disappearance of the infection from the genito-urinary system and marked reduction, but not elimination, of the *Chlamydia trachomatis* and Cytomegalovirus infections, Hg, deposits, and increased Uric acid in the pancreas.

During a strong recurrence of the *Chlamydia trachomatis* which coincided, as it often does, with a sudden change in environmental temperature, a treatment course with Doxycycline was begun together with various drug uptake enhancements. It was known at this time to the inventor that in response to treatment *Chlamydia trachomatis* retreats to 3 small areas: the sublingual caruncle, the L. and R. axillae, and the genitals, (2 additional areas were located later), and that Hg and elevated Uric acid levels would be found in these infected areas because of the apparent protection of the Chlamydia from the antibiotic by Hg. Therefore Chinese parsley tablets, 100 mg, 4 times/day, were added to the treatment to eliminate the Hg, with Doxycycline, 100 mg twice daily to combat the *Chlamydia trachomatis* and drug uptake enhancement to deliver both substances to the infected areas. Doxycycline became the drug of choice when it was determined by the Bi-Digital O-Ring Test for drug compatibility that it had no mutually canceling effect with EPA/DHA and was equally, if not more, effective than the more traditionally used antibiotics. Within one week a thorough examination with the Bi-Digital O-Ring Test revealed that the *Chlamydia trachomatis* had migrated to the 3 specific areas named above. At the end of one more week of treatment the *Chlamydia trachomatis* and Hg deposits had been eliminated, and Uric acid had returned to normal level in all the 'hiding places'. All symptoms disappeared. Treatment was continued for an additional week after which there was no recurrence of symptoms or infection in the following 3 months.

Clinical Case 3

A 30 year old Asian-Brazilian female gastroenterologist had intractable diarrhea for about 2 years. Repeated laboratory tests were done but her physicians did not find the cause, or determine effective treatment. When she was examined with the Bi-Digital O-Ring Test, there was strong response to *Chlamydia trachomatis* infection in the colon and urinary bladder. There was presence of abnormal Thromboxane $B_2$ which indicates marked microcirculatory disturbance. Localized Hg deposits and abnormally elevated levels of Uric acid were also found. Based on prior experience, these findings, particularly the presence of Thromboxane $B_2$, indicated that no antibiotic would be able to reach the infected area. In addition, previous studies have indicated that even if effective drugs can reach the pathological area, localized deposits of Hg inhibit their potential therapeutic effects. Therefore Chinese parsley tablets, 100 mg, were given 4 times/day together with Doxycycline (100 mg) twice daily. Choice of effective medications and the dosages were determined by the Bi-Digital O-Ring Test. However, ½ hour after the antibiotic and dietary supplement were given, the Bi-Digital O-Ring Test revealed they were not present in the areas of infection. For this reason strong Shiatsu massage of 1–2 minutes duration on the representation areas of the gastrointestinal and genito-urinary systems on both hands was done for drug uptake enhancement. At least 1 cup of water was taken with each of the 4 daily doses of Chinese parsley tablets since these have a diuretic effect. This treatment was continued and about 3 days later the diarrhea had almost disappeared and the Bi-Digital O-Ring Test revealed that the *Chlamydia trachomatis* infection was virtually gone, as were the Hg deposits. Uric acid had returned to normal levels. Despite the rapid disappearance of symptoms, treatment was continued for a total of 14 days to make sure that the Chlamydia was totally eliminated. At the end of that time period the subject reported that she was symptom free.

Clinical Case 4

A 40 year old Asian-American male chef has had frequent appearances of red, itchy rashes on his chest, back, hips, and left scrotum since the age of 3, for which he was examined by many internists and dermatologists who considered the condition to be caused by food allergies, treated it symptomatically, but were not able to eliminate it. Whenever there was a dramatic change in the environmental temperature such as sudden heat waves, or extreme cold, the rash reappeared. He was diagnosed as having *Chlamydia trachomatis* by a standard laboratory blood test several years ago, but because he was known to have abnormal liver function, his physician was hesitant to prescribe antibiotics like Erythromycin since *Physicians' Desk Reference* warns of possible liver damage as a side effect. When he was finally seen by the inventor 2 years ago, strong *Chlamydia trachomatis* response in the genito-urinary system was found by the Bi-Digital O-Ring Test, which also showed that Erythromycin was not only not harmful to the liver, it appeared to be potentially beneficial. Therefore treatment with Erythromycin, 500 mg 4 times daily with (+)Qi Gong energy stored paper applied to the cardiovascular representation area on the scalp over the cardiovascular representation area of the Medulla Oblongata for drug uptake enhancement.

After 14 days the symptoms had improved but the infection was still moderately strong according to the Bi-Digital O-Ring Test, despite textbook claims that that treatment time period of 2 weeks should be sufficient. This subject, as others I have treated, required about 3 months for the *Chlamydia trachomatis* infection to be eliminated from the affected, symptomatic areas. But subsequently, during a period in which there was a rapid and dramatic change in the environmental temperature, the infection returned. A 5 day treatment of Azithromycin was given which proved to be more rapidly effective than the Erythromycin had been in diminishing the localized infections. However, since the rash shifted to the face, an additional week of the treatment was given. Re-examination at the end of that period revealed diminished symptoms, but the *Chlamydia trachomatis* had retreated to the following areas: the sublingual caruncle, R. & L. axillae, genitals, and the horizontal lines above and below the knees at which Insulin-like Growth Factors are found. Significant Hg deposits and elevated levels of Uric acid were also found in these areas.

A few months after the apparently successful treatment, the subject requested re-examination because of the return of his previous symptoms during rapid change of environmental temperature. There were large circular areas of rash with multiple small red papules which had strong positive response to *Chlamydia trachomatis* and caused severe itching on the skin on his left chest and covering both scapula on his back. Bi-Digital O-Ring Test indicated strong response to *Chlamydia trachomatis* in these areas as well as in the 6 places previously described to which *Chlamydia trachomatis* commonly retreats, i.e. at the sublingual caruncle, in both L. and R. axillae, in the genitals, the maxillary and/or ethmoid & frontal sinuses with small part of nostrils, and the Insulin-like Growth Factor 1 & 2 positive horizontal lines above and below the knees. Response to *Chlamydia trachomatis* by Bi-Digital O-Ring Test was measured at (+6) on the left side of the genitalia, and at (+1) on the right. Localized Hg deposits and abnormally elevated Uric acid were also found in the areas where Chlamydia response was positive. Bi-Digital O-Ring Testing for most effective medication indicated that Erythromycin was no longer the drug of choice because of markedly reduced effectiveness, but found Doxycycline, 500 mg to be most desirable. Chinese parsley tablets, 75 mg, 4 times a day, were also given to remove the localized Hg deposits with drug uptake enhancement methods. 24 hours later Bi-Digital O-Ring testing revealed that *Chlamydia trachomatis* response was reduced to (+1) on the chest and back, but remained very strong (+6) on the left side of the genitals, and increased to (+4) on the right side of the penis. Response to *Chlamydia trachomatis* at the sublingual caruncle and in the L. and R. axillae was still (+6).

Three days later re-evaluation showed the following response to *Chlamydia trachomatis*: Sublingual caruncle: (0); Maxillary sinus (0); L. and R. axillae: (0); L. side of genitals: (+1); R. side of genitals: (+6). Response on both sides of the chest and back remained at (+1). Investigation of drug uptake revealed that the antibiotic was not reaching the area of maximum response, (+6) on the right side of the genitals. The correct procedure of directing the beam of a hand-held battery operated flashlight to the representation area for the penis on the right hand was done by the patient with supervision. This drug uptake enhancement procedure immediately sent the antibiotic to the targeted area as was shown by maximal resonance between the Doxycycline in the right side of the penis and a capsule held as a control.

Treatment with such drug uptake enhancement was continued for the next week. The remaining responses to *Chlamydia trachomatis* found were strong resonance (+5) in a previously unexamined area, the face, particularly between the hairline and the upper jaw, an area which includes the frontal, ethmoid and maxillary sinuses and small part of nostrils, which had by this time, been identified as the 5th place to which the *Chlamydia trachomatis* retreats, moderate response (+4) in the nose, ears, and sublingual caruncle, and weak response (+2) in the axillae and R. side of the genitals. Using both of the drug uptake enhancement methods of Shiatsu massage to the representation areas on the hands and the beam from a battery-operated flashlight applied to the occipital area of the scalp over the cardiovascular representation area of the Medulla Oblongata after taking the antibiotic and Chinese parsley tablets 4 times/day was recommended.

The subject was seen again 10 days later, 20 days after the onset of treatment. All the previously infected areas showed lack of resonance (+0) to *Chlamydia trachomatis* by Bi-Digital O-Ring Test. Scanning of his entire body showed that the only areas of positive response were at the horizontal growth lines above and below both knee joints. As my previous tests indicated, strong positive resonance with Insulin-like Growth Factors is found at these lines under normal conditions. In this subject Insulin-like Growth Factors were markedly diminished in the middle third of the lines where (+2) response to *Chlamydia trachomatis* also existed. Drug uptake enhancement was now concentrated on these areas and also the genitals since experience has shown that aggressive treatment of the surrounding area, including other 'hiding places' is necessary in addition to treating the targeted area, to surround the micro-organisms and prevent their migration.

Twenty-eight days after the initiation of treatment, *Chlamydia trachomatis* response in the entire body including in the last 'hiding place' in the Insulin-like Growth Factor positive horizontal lines above and below the knees had disappeared. The abnormal localized Hg deposits had also been eliminated and the Insulin-like Growth Factors which had been reduced in the presence of infection had now returned to normal levels.

Clinical Case 5

A 59 year old female Asian-American business executive was diagnosed as having *Chlamydia trachomatis* and *Lyme Borrelia burgdorferi* 2 years ago prior to having surgery for a R. knee joint replacement, made necessary by severe rheumatoid arthritis. Both *Chlamydia trachomatis* and *Lyme Borrelia burgdorferi* were treated with the limited goal of eliminating infection in the R. knee so that the surgery would not spread it. Treatment consisted of Erythromycin, 500 mg, 4 times/day with several transcutaneous electrical stimulation sessions with 1–2 pulses/second, and (+)Qi Gong energy stored paper application on the cardiovascular representation area over the Medulla Oblongata in the occipital area of the skull. After several weeks of this treatment, *Chlamydia trachomatis* and *Lyme Borrelia burgdorferi* infections were completely eliminated from the R. knee joint and the last 'hiding place', the Insulin-like Growth Factor positive horizontal lines above and below the knees. Subsequently knee joint replacement surgery was performed successfully without any complications.

About 1 year later the patient again sought consultation because of pain that had developed in her L. knee and the joints of the hands and feet. The Bi-Digital O-Ring Test revealed strong generalized response to *Chlamydia trachomatis* and *Lyme Borrelia burgdorferi*, (+6), with localized Hg deposits in the areas infected with *Chlamydia trachomatis*. It was decided to treat the *Chlamydia trachomatis* first to determine by the process of elimination which of the coexisting infections was the major cause of the pain. Treatment consisted of Doxycycline, 100 mg, with Chinese parsley tablets, 75 mg, and the light beam from a battery-operated flashlight applied to the occipital area over the cardiovascular representation area of the Medulla Oblongata 4 times/day to direct and enhance drug uptake.

Three days later, re-evaluation with the Bi-Digital O-Ring Test showed markedly reduced response to the monoclonal antibody of *Chlamydia trachomatis* as follows: Mild response, (+1) in the L. eye, R. ear, R. nostril, and R. knee, and (+2) in the L. ear, L. nostril, and L. knee. Stronger response was found in the 4 specific locations the *Chlamydia trachomatis* appears to seek out to avoid the antibiotic: (+6) at the sublingual caruncle, in the vagina, and in the L. axilla; and (+3) in the R. axilla. There was strong response in the ankles (+6) as well. Investigation of drug uptake phenomena revealed that the Doxycycline and Chinese parsley did not reach the lower legs while the subject was wearing her metal rimmed eyeglasses. The metal earpieces which had only a thin coating of plastic over the hooked ends contacted the undersides of the foot representation areas on the R. and L. pinnae, interfering with microcirculation and inhibiting drug uptake. Thicker plastic coverings were applied to the earpieces which caused immediate increase in drug uptake in the lower extremities from the knee below the patella to the toes.

Treatment was continued for another week after which the Bi-Digital O-Ring Test revealed complete elimination of the *Chlamydia trachomatis* infections from all parts of the body except at the Insulin-like growth factor positive horizontal lines above and below both knee joints where (+2) response to *Chlamydia trachomatis* existed. In the presence of *Chlamydia trachomatis* and *Lyme Borrelia burgdorferi* infections co-existing Insulin-like Growth Factors were also markedly diminished (+2–3). Drug uptake enhancement was now concentrated on these areas and also the genitals since experience has shown that aggressive treatment of the surrounding area, including other 'hiding places' is necessary in addition to treating the targeted area, to surround the microorganisms and prevent their migration.

Eighteen days after the initiation of treatment, *Chlamydia trachomatis* response in the entire body including in the last 'hiding place' in the Insulin-like Growth Factor positive horizontal line above and below the left knee had disappeared. The abnormal localized Hg deposits had also been eliminated and the Insulin-like Growth Factors which had been reduced in the presence of infection had now returned to normal levels. Amoxycillin, 500 mg. 4 times/day was prescribed to now treat the Lyme Disease in her left knee, wrists, and in all the areas to which micro-organisms have been observed to retreat.

Clinical Case 6

A 57 year old white American female research assistant attended a crowded rally at Madison Square Garden where she had to wait for many hours to get in on an icy day. The following day she found it difficult to concentrate at work, and asked the inventor to examine her because of the pain she felt in the occipital area of her head. Bi-Digital O-Ring test examination showed strong *Chlamydia trachomatis* infection (+6) with Uric acid increase (20 mg/dl) and Hg deposits on the whole left side of the head. The effective antibiotic was found to be Doxycycline, 100 mg, given twice a day with 100 mg of Chinese parsley tablet 3 times/day and drug uptake enhancement using strong Shiatsu stimulation of the organ representation areas corresponding to the head on the distal phalange of the middle fingers. Two days later response to *Chlamydia trachomatis* infection in the head disappeared but there was strong positive response for *Chlamydia trachomatis* (+6) and Hg in 3 of the areas to which these infections retreat: the sublingual caruncle, left and right axillae, and the vagina near the orifice of the urethra. Treatment was continued with drug uptake enhancement focused on these areas. A transitory relapse occurred however when the subject was exposed to freezing weather for 4 hours without adequate winter boots.

Twenty-two days later, on reexamination infection had disappeared from the 3 areas that had been treated, but a strong response to *Chlamydia trachomatis*; and Hg was found in the face. At that point, the *Chlamydia trachomatis* positive areas of the face were mapped where there were also markedly increased localized mercury deposits. The *Chlamydia trachomatis* and Hg existed not only in the maxillary, ethmoid & frontal sinuses, small part of nostrils and the bridge of the nose, but also in the periorbital muscles, the muscles surrounding the eye which often modify facial expression. Twenty-six days later, the only Chlamydia positive areas were the Insulin-like Growth Factor positive horizontal lines above and below the knees (in which the Growth Factors were abnormally reduced). The degree of the response was rather weak (+1).

Twenty-eight days from the onset of treatment, all symptoms had disappeared. Bi-Digital O-Ring Test response to *Chlamydia trachomatis* and Hg was negative, and the Growth Factors had returned to normal levels.

Clinical Case 7

An approximately 45 year old, white Brazilian female Rheumatologist has had pain in her shoulders, elbows, wrists and finger joints for the past 15 years. The pain became so severe during the 6 months before she was examined by the inventor that she found it difficult to button her clothing, drive her car, and pursue her clinical practice. Examination with the Bi-Digital O-Ring Test revealed Herpes Simplex Type I infection starting at the 1st cervical and extending to the 12th thoracic vertebra on the right side. The infection was distributed from the midline, of the spine across the right side of the body to the front midline. On the corresponding left side of the body, Herpes Simplex Type II infection was found. Localized deposits of Thromboxane $B_2$ and Hg were found on both sides. The Bi-Digital O-Ring Test indicated that Sundown EPA, 180 mg, with DHA, 120 mg, and Chinese parsley tablets, 100 mg, taken 4 times/day was the most potentially effective medication. Two drug uptake enhancement methods were used. Strong Shiatsu massage of 1–2 minutes duration on the representation areas for the upper extremities on both hands was combined with application of stored (+) Qi Gong energy paper for 1 minute to the cardiovascular area at the back of the head over the Medulla Oblongata after taking medication. Three days after treatment began the symptoms were significantly reduced. Two weeks later she was again able to drive her car since most of the pain had disappeared.

Clinical Case 8

A 28 year old, white American male cleaning supplies salesman presented with a 4 year history of severe pain in both feet and mild pain in the legs up to the knee. He had been examined by podiatrists, orthopedic surgeons, neurologists, chiropractors and gout specialists but no specific cause of the pain was found. Examination with the Bi-Digital O-Ring Test revealed Herpes Type I infection in the right foot and leg to the hip and extending to the lumbar vertebrae, and Type II in corresponding areas on the left. Presence of Thromboxane $B_2$ and localized Hg deposits were also indicated by the Bi-Digital O-Ring Test. Treatment consisted of EPA, 180 mg, with DHA, 120 mg, 4 times daily with exposure to a battery-operated flashlight beam for 1 minute to the foot and leg and on both hands (both surfaces of the thumbs and little fingers) for drug uptake enhancement. The subject drank a soup made of chopped cilantro 4 times daily to eliminate Hg. After about 2 weeks of treatment the symptoms still persisted. When reevaluated, the Herpes virus was unchanged leading the inventor to suspect that the drug was probably not reaching the infected areas. The subject was told to continue the EPA with DHA and reinstructed in drug uptake enhancement, using strong pressure on the appropriate representation areas on the fingers with the opposite thumbnail for about 30 seconds to 1 minute. He was also given a 4 day supply of Chinese parsley tablets, 75 mg, to clear the Hg deposits. He followed this treatment plan for 4 days, but then suspended it, since he had his wisdom teeth extracted, was taking Ledercillin as prescribed by his dentist, and wanted to avoid possible drug canceling interactions.

He was seen again one day after completing the course of Ledercillin. Again there was no decrease in symptoms or viral infection in the lower extremities, once more raising questions about the maintenance of the effective antiviral agent in the infected areas for a sufficiently long period of time to be therapeutic. I decided, after confirming that the EPA/DHA had reached the infected areas with drug uptake enhancement, to test at 5 minute intervals to see how long it remained. Within 5 minutes there was markedly diminished drug uptake in the lower extremities. It was then necessary to determine what was causing this inhibition of drug uptake in order to treat the infection. Suspecting electromagnetic field interference, I asked the subject to remove any credit cards with magnetic strips from his pockets, and his watch, rings, or decorative chains around his neck, all of which have been demonstrated to interfere with drug uptake, but, having already been cautioned during his previous visit, he had none of these items. The only metal he was wearing was in the frames of his glasses. When he took them off, uptake of the antiviral agent immediately increased in the infected lower extremities. When I checked to see the exact place the eyeglass frames were contacting his ears, I noted that it was directly behind the representation areas for the feet at the top of the pinnae (outer ears). I found that wrapping plastic around the ends of the metal arms of the glasses frames acted as insulation preventing inhibition of drug uptake to the feet. The subject stated his intention of putting heavy plastic grips over the ear pieces and continuing the previous treatment.

Clinical Case 9

The inventor, a 61 year old Asian-American male, had a toothache in his upper right incisor. Bi-Digital O-Ring Testing of the root of the tooth showed Alpha-Streptococcus infection which was sensitive to Wyeth Amoxycillin, 500 mg, which was therefore given 4 times/day with drug uptake enhancement. The test also indicated absence of viral infection since there was no sensitivity of the infection to EPA/DHA, a strong antiviral agent. After 2 days of treatment, the sharp pain had diminished to a persistent dull ache. I saw a dentist who injected local anesthesia, opened the root canal, removed the nerve and blood vessels, placed formaldehyde inside the root canal as an antiseptic, and sealed it temporarily. Shortly after this procedure the pain not only became more severe, but the painful area increased in size moving toward the roots of the neighboring teeth and across the cheek to the temporo-mandibular joint. Bi-Digital O-Ring Test indicated reduced bacterial infection; therefore the formaldehyde was suspected to be an additional irritant to the residual infection. Testing was done to see if formaldehyde existed in the painful areas using pure formaldehyde as a reference control substance. The test indicated strong resonance with formaldehyde in the entire painful area, from the root of the teeth to the cheek, suggesting that the formaldehyde placed in the root canal of the right incisor had leaked out and spread. At this time I was reported irritability and difficulty retrieving a few commonly used names in conversation several times a day. Such word-retrieval difficulty is commonly seen in patients who have viral or bacterial infection of the hippocampus.

Further examination with the Bi-Digital O-Ring Test revealed that the Alpha-Streptococcus infection had diminished in the root of the tooth, but had spread with tenderness to the temporo-mandibular joint. Cytomegalovirus infection also from the site of the injection near the root of the tooth extended across the right cheek then upward to the hippocampal area of the brain on the right side. There were significant local deposits of Hg in the Cytomegalovirus positive area. There is a strong likelihood that the Cytomegalovirus infection was introduced from the site of injection by the injection needle used to introduce the local anesthetic because of insufficient sterilization of the injection site. I was treated with EPA, 180 mg, and DHA, 120 mg, 4 times/day to treat the CMV; Wyeth Amoxycillin, 500 mg, 4 times/day for the Alpha-Streptococcus, together with Chinese parsley tablets, 100 mg to clear Hg; with drug enhancement provided by strong Shiatsu massage of the organ representation areas for the right hippocampus on the tip of the middle fingers of both hands. Within 2 days of this treatment, CMV infection in the hippocampal area disappeared as did the mild word-retrieval difficulty. The subject returned to the dentist who removed the formaldehyde packing from the root canal which he then widened and irrigated repeatedly. Before the dentist sealed the canal, using the Bi-Digital O-Ring Test, I found that there was no longer a positive resonance with a minute amount of pure formaldehyde, the reference control substance.

A few days later the subject noticed a recurrence of the mild word-finding difficulty. Examination of the face and brain with the Bi-Digital O-Ring Test indicated strong Cytomegalovirus infection in the area surrounding the root of the problem tooth, extending horizontally across the right cheek to the area in front of the ear lobe, then upward to the right side of the head over the hippocampal area. I resumed the antiviral treatment done previously. Twelve hours later I found that the degree of viral infection over the hippocampus was reduced, but it remained strong on the right side of the face. Treatment was continued this time using strong Shiatsu massage not only on the hippocampus representation areas on the middle fingers, particularly the R. middle finger, but also on the representation areas for the face, specifically the right teeth on the 1st phalange of the right middle fingers. I also took an optimal dose, established by the Bi-Digital O-Ring Test, of fresh carrot-green extract as a potential Hg removing agent since the Cytomegalovirus infected area also showed local deposits of Hg. The inventor had recently hypothesized that since carrots are members of the parsley family (Umbelliferae), the extract of the carrot-green leaves might have a similar effect to that of Chinese parsley, (cilantro), in eliminating deposits of Hg, Pb, or Al coexisting with infection in the tissues. Alcohol was used to extract the effective component from the carrot-greens and was then allowed to evaporate. Testing urine samples for Hg before and after taking the extract indicated that carrot-green extract does have a similar effect to Chinese parsley.

Three hours after taking the EPA/DHA as an antiviral agent together with carrot-green extract and using strong Shiatsu massage on the organ representation areas for the right side of the face and brain on the distal phalange of the right middle finger, infection on the right side of the face diminished moderately, but within 6 hours Cytomegalovirus infection appeared on the left side of the brain in the hippocampal area with localized Hg deposits. and the subject noticing irritability. I interpret this migration of the viral infection from the right to the left side of the brain to have occurred because of the high concentration of the antiviral agent in the right cerebral hemisphere and the very low concentration left side of the brain. The Cytomegalovirus, also retreated to the sublingual caruncle, the left and right axillae, the maxillary, ethmoid and frontal sinuses, the nose and ears. Twelve hours later the virus was gone from the sublingual caruncle but it was observed that the virus was moving into adjacent regions whose representation areas had not been stimulated for drug uptake enhancement, like the ears. Therefore strong Shiatsu massage of the middle finger was extended to include the sides of the distal phalange for the ears, and the proximal phalange of the index and ring fingers on the palm side for the axillae. The treatment was then continued for another 2 days after which all symptoms and response to the monoclonal antibody of the Cytomegalovirus had disappeared.

About 1 week after the second visit to the dentist severe pain started at the root of the upper right cuspid, the tooth next to the lateral incisor which was the original site of infection, with redness and swelling of the gum. An X-ray was taken of right upper cuspid after root canal was opened and metal wire was inserted to estimate the distance from the apical foramen. This was taken about 3 weeks after right upper incisor root canal treatment was performed. There existed a pathological darkening of the area about 5 mm from apical foramen extending up the dentine, cementum & periodontal membrane and surrounding area. Bacterial infection and marked deposit of mercury co-exists but antibiotic, Wyeth arnoxicillin which was taken at that time did not reach this infected area in spite of vigorous drug uptake enhancement. Examination using Bi-Digital O-Ring Test on the root of the tooth indicated strong bacterial infection and also indicated Wyeth Amoxicillin, 500 mg to be potentially very effective. The dentist injected local anesthesia into the oral tissue, opened the root canal to release the pressure and remove the infected tissue, nerve and blood vessel, and after sterilizing the canal, temporarily filled with Gutta Percha without using formaldehyde. Before filling the root canal with Guttal Percha, a second X-ray was taken while a metal probe was temporarily placed in the opened root canal. The X-ray showed recognizable change of density, in the tooth with the open root canal, 5 mm from the apical foramen up the dentine, cementurn and periodontal membrane, and in these areas there was a marked deposit of mercury and alpha streptococcus infection. This infection did not appear on the X-ray taken at the very 1st visit for original tooth but about 5 weeks later it extended to the periodontal area near the root and entire body of the tooth within 5 mm from the tip of the root canal.

Two days later the subject experienced irritability, diminished short-term memory, and mild, transient, word-retrieval difficulty a few times a day. The Bi-Digital O-Ring Test again showed Cytomegalovirus infection with Hg deposits in the right side of the face and head starting from near the roots of the involved teeth and spreading to the TMJ, and R-Hippocampal area. For this viral infection, a mixture of DHA, 180 mg with EPA, 120 mg as an antiviral agent 4 times/day, and 100 mg of Chinese parsley tablets 3 times/day to remove localized Hg deposits were given with drug uptake enhancement by both strong Shiatsu massage to the representation areas for both sides of the brain (on the upper part of the distal phalange of both middle fingers), and light from a battery-operated flashlight held directly on these organ representation areas on the fingers or on the occipital area of the skull over the cardiovascular representation area of the Medulla Oblongata. Six days later the Cytomegalovirus infection had disappeared not only from the original sites, but all five 'hiding places' were also virus free. Although I no longer experienced the mild cognitive symptoms caused by the Cytomegalovirus infection of the hippocampal area, Alpha streptococcus infection with dull pain persisted in the roots of the two teeth despite treatment with Wyeth Arnoxicillin, 500 mg, 4 times/day, with drug uptake enhancement for almost one month.

Twice previously I had similar dental pain in the lateral part of the oral cavity with alpha streptococcus infection and loose teeth; the previous dentist suggested that the tooth be extracted, but he refused. Using Wyeth Amoxicillin 500 mg which was found to be most effective for the infection by Bi-Digital O-Ring Test, and with (+)Qi Gong energy stored paper, taped above infected area for a few days, used as a drug uptake enhancement, these problem teeth are still remaining without much problem and looseness firmed up when infection disappeared.

The persistence of this bacterial infection may be explained by the fact that the removal of the blood vessels and nerves from the root canal make treatment of the infection difficult if not impossible. Normally drug uptake enhancement methods increase delivery and uptake of drugs in infected areas in which nerves and blood vessels exist. Since these structures are necessary for drug delivery and maintenance at therapeutic levels in the pathological area, infection remained in a sealed root canal becomes chronic and a potential source of further infection even if extensive drug uptake enhancement methods are used. It is therefore advisable to treat infection vigorously with suitable antibiotics using drug uptake enhancement methods before root canal procedures are done, before the nerve and blood vessels are removed.

I have now started to use combination of more powerful drug uptake enhancement method including Krypton bulb DC battery operated flashlight with red filter and pasting of Qi Gong energy stored paper or bandaid. Antibiotics began to reach the pathological area and mercury began to decrease.

Clinical Case 10

A 40 year old white American female homemaker experienced severe pain on both sides of her upper back and shoulders for about 1 month prior to examination. Evaluation with the Bi-Digital O-Ring Test indicated strong response to Herpes Simplex Type I virus infection on the right side and Herpes Simplex Type II virus on the left. There were significant localized deposits of Hg coinciding with the virus infected areas. She was treated with EPA, 180 mg, and DHA, 120 mg; Chinese parsley tablets, 75 mg; and strong Shiatsu massage of the organ representation areas for the back and shoulders on the hands all 4 times/day. Within 24 hours the infection and most of the symptoms had disappeared. This treatment was continued for about 5 days after which the subject reported nearly complete cessation of symptoms. Two weeks later she remained symptom-free and treatment was discontinued.

Clinical Case 11

A 61 year old Asian-American male physician went shopping for groceries on a very cold, snowy, windy day, and while carrying back a full bag (about 10 kg each) in each hand he suddenly developed a sharp pain in the left chest in the area of the heart, with the pain radiating towards the left side of the neck. The pain diminished when he stopped and bent his head and chest forward, but still, significant pain persisted. When he applied strong Shiatsu massage to the heart representation areas on proximal phalange on the middle fingers of his hands, and to the acupuncture point Shen Men (Pericardium 7) in the palm side of the wrist at ulnar side for about 1 minute each to increase microcirculation to the heart, the chest pain subsided after 5 minutes. About 10 minutes later at home, the chest pain had almost disappeared, but he felt very fatigued and lay down to rest. Ten minutes later when he tried to stand up, he couldn't because of a sharp pain in the lower left lumbar region which increased when he bent in any direction. The pain was minimal on sitting or standing erect. Examination with the Bi-Digital O-Ring Test revealed Herpes Simplex Type I infection with marked localized Hg deposit in the area of lumbar vertebrae 4 & 5 which corresponded to the painful area, and Herpes Simplex Virus Type II with moderate localized Hg deposit in the left chest wall covering the heart where he had experienced the pain. However, none of the 5 hiding places were found to have any infection.

Since he had not had such infections within the previous weeks, possible sources of viral infection were considered. Two days before this sudden pain started a neurologist asked him to examine a patient who had had intractable lower back pain for more than 2 years, corresponding to the 4th and 5th lumbar vertebrae. Bi-Digital O-Ring Test revealed that she had Herpes Simplex Type I with localized Hg deposits on the left side of her body, and Herpes Simplex Type II on the right side. The subject had spent almost 2 hours in close proximity to that patient.

For these viral infections, a mixture of DHA, 180 mg with EPA, 120 mg, as an antiviral agent 4 times/day, and 100 mg of Chinese parsley tablets 3 times/day to remove localized Hg deposits were given. Both strong Shiatsu massage to the representation areas for the lower back (on the back of the hands) and the chest (at the proximal phalange of the middle finger) as well as their surroundings, and a red light beam from a battery-operated flashlight with brighter Krypton bulb with a red filter held directly on these areas or on the cardiovascular representation area over the Medulla Oblongata on the occipital area of the skull were done for drug uptake enhancement. Within 2 days, most of the pain and the infections had been eliminated. Since the symptoms disappeared in response to the treatment so quickly, he did not have a chance to go for X-rays or ECG.

He had had a similar problem before, not in winter extreme cold, but on a hot summer day. The first incident occurred when he was about 35 years old when he made a sudden movement to turn a baby stroller. After 2 weeks of bed rest at home without any improvement in the sharp pain that occurred with any movement of the lumbar area, he was admitted to a hospital affiliated with a medical school for an additional two weeks of traction for a herniated disc under the care of an orthopedic surgeon. In most of the patients with severe back pain with demonstrable herniated disc by MRI, the Bi-Digital O-Ring Test often shows viral or bacterial infection in the herniated disc or surrounding vertebrae and sometimes within the spinal cord, and when effective antibiotics are given with drug uptake enhancement methods, pain often disappears or markedly diminishes. Often the herniated disc still appears on the MRI after disappearance of the pain, however maintaining proper posture, especially when bending or lifting, often resulted in the gradual disappearance of the herniation of the discs. Such findings suggest that when disc herniation coexists with infection and localized Hg deposits, inflammation and subsequent swelling caused by the infection contribute to increased pressure intensifying pain.

Additional clinical applications to various chronic problems such as the treatment of psoriasis and hypertension has been observed.

A 43-year old white male attorney suffered from severe psoriasis of upper and lower extremities and trunk of the body for the past 20 years. Reddening and flaking of the skin and frequent bleeding appeared often after stress; however, psoriasis was not noticably visible in the face, neck, and hands, where skin is constantly exposed to the sun. In the past, the only treatment which was distinctly helpful in reducing symptoms was the administration of steroid hormones, but because of the side effects, he no longer uses steroid hormones. Upon examination of the psoriasis of the patient, the applicant noticed there was a viral infection and significant localized mercury deposits only in the skin with psoriasis. Because of this, about 5–8 grams of Chinese parsley, which was homogenized and dried and put into a capsule (dry weight is reduced to about one-tenth of the original fresh parsley). Originally, this dose was recommended three times a day along with a mixture capsule of EPA 180 mg and DHA 120 mg as antiviral agent four times a day with drug uptake enhancement, but the patient took the Chinese parsley only two times a day. However, within two weeks significant improvement by reduction of the redness and flaking of the skin and bleeding and patient claims about 50% improvement compared with pre-treatment condition.

A 59-year old white female had flu-like symptoms with sneezing of the nose and suddenly developed occipital headaches and became very irritable. Upon examination, both diastolic and systolic blood pressure was increased 180/105 mm Hg. Also, there was a herpes simplex type I infection in the right side of the occipital area, particularly left ventricular representation area of the medulla oblongata and herpes simplex type II infection in the left side of the occipital area, particularly in the right ventricular representation area of the medualla oblongata with localized deposits of both Hg and Pb at both the right and left side of the medualla oblongata. Her blood pressure was normal at least for the previous one year. To remove Hg and Pb, a Chinese parsley tablet was given 3 times a day, and for viral infection, a mixture of the EPA 180 mg with DHA 120 mg was used 4 times a day as antiviral agent. However, both substances never reached the infected medulla oblongata. To enhance drug uptake, red light radiation from a high intensity krypton lamp flashlight with red filter was applied directly at the occipital area of the medulla oblongata, which resulted in the marked drug uptake in the virus-infected medulla oblongata and heavy metals were excreted rapidly in the urine, and blood pressure dropped to normal within 2 days.

Many infectious diseases commonly designated as sexually transmitted are often spread through other channels. *Chlamydia trachomatis* and some Herpes family viruses can be transmitted by contact with infected saliva left on non-sterilized dishes, silverware, cups and glasses if any open wound exists on the lips or in the mouth. Another common but generally unrecognized source of infection is injection of local anesthesia through an incompletely or non-sterilized injection site in the oral cavity which introduces microorganisms from the surface deep into the tissue from where they can travel to the same side of the brain causing distractibility, irritability, confusion, word-retrieval difficulties, and/or short term memory loss. Although this inventor was able to trace the source of original infection to the site of injection, (in a number of our patients), it is often difficult to link such infection with the dental procedure since signs of infection may not appear for at least several days to a few months post local anesthesia injection. It is highly desirable for dentists to sterilize the injection site of the oral cavity thoroughly before injecting local anesthesthetic agent to prevent such infections. The widespread nature and frequent recurrence of common infections caused by various micro-organisms makes effective, affordable treatment a priority.

Although the role of infection in chronic back pain is generally believed to be minimal (less than 1%), clinical experience indicates that more than 80% of patients examined for back pain using the Bi-Digital O-Ring Test have either viral, bacterial, or a combination of infections existing in the lumbar vertebrae, intervertebral discs, or in the spinal cord. The most common cause of intractable pain is Herpes Simplex Type I and or Herpes Simplex Type II infection(s). Even when effective antiviral agents are given, they will often not reach the infected area unless drug uptake enhancement methods are used regularly. However, localized Hg deposits which coexist with these infections, appear to protect them from the otherwise effective antiviral agents making elimination of such metals a necessary first step in treatment.

*Chlamydia trachomatis* infection is one of the most widespread diseases in the world. If untreated, it can lead to genito-urinary problems, infertility, blindness, intractable joint pain, chronic respiratory difficulties and other debilitating conditions. Similarly Herpes Family viral infections, particularly Herpes Simplex Types I and II, are major causes of intractable headache and pain in various other parts of the body, and Cytomegalovirus is a major but unrecognized cause of many incapacitating brain diseases, including Parkinson's Disease.

Treating *Chlamydia trachomatis* in the past with effective antibiotics such as Erythromycin, Azithromycin, or Doxycycline, together with drug uptake enhancement for a few weeks often improved the symptoms by eliminating the infection locally as is generally believed. But in this inventor's experience, such treatment fails to eliminate it from the body completely. To eliminate the infection locally, the inventor found it necessary to apply various drug uptake enhancement methods such as Shiatsu massage, light beam from a battery-operated Krypton flashlight with red filter, (+) Qi Gong energy stored paper, (−) electrical field stimulation, low pulse repetition rate electrical stimulation, South pole magnetic field stimulation, acupuncture, to the specific organ representation areas of the infected parts of the body on the hands, scalp, feet or ears adjacent to those organ representation areas. Such stimulation delivers the medications to the surrounding, as well as the infected, area preventing the micro-organisms from escaping to less intensively medicated areas. This inventor's clinical experience has demonstrated that when drug uptake is enhanced solely in the infected area, the micro-organisms often migrate to neighboring parts of the body where little antibiotic medication exists. Such a shift was often observed within the space of several hours, as in Clinical Cases 1 and 9 discussed herein. In Case 1, CMV was treated with the effective antiviral and Hg removing agents supported by drug uptake enhancement directed specifically to the nose. The CMV disappeared from the nostrils, but promptly migrated to the ear canals as the representation area for the ears had not been included in the drug uptake enhancement procedure. In Case 9, the infection when treated with drug enhancement to the right side of the brain, moved within 6 hours to the left side of the brain.

Applying light beam to the organ representation areas is a quick and convenient drug uptake enhancement method. Red spectra from a light-emitting diode, red monochromatic Laser beam, and light exposure from both a DC battery flashlight with or without red filter and an AC lamp light bulb, as well as fluorescent light on specific organ representation areas on the hands were compared for their effects on localized drug uptake. It was found that an inexpensive red broadspectra light emitting diode was at least equally effective for drug uptake enhancement as a Laser beam of comparable output, but that fluorescent light inhibits drug uptake and should therefore be avoided. Both the red light from a pen light covered with a red filter, and the white light from a plastic, battery operated regular flashlight or brighter Krypton flashlight if held still and beamed at an organ representation area and its surrounding area enhanced drug uptake not only in the specific organ, but also in the surrounding area. Light beam through red filter (very thin 0.198 gauge red 'decorative cellophane' by Hygloss Products, Inc., Wayne, N.J. 07470, used as double layer satisfactorily functioned as a red filter) from these flashlights had more effective drug uptake enhancement and prolonged effective duration. However, light beam from a battery-operated Halogen high intensity flashlight inhibited drug uptake and may be potentially harmful.

The following common objects are among the many which inhibit drug uptake: eye glasses, specifically lightly coated metal ear pieces which contact the underside of the representation areas on the ears for the feet and lower legs, credit and/or other plastic cards carried in a pocket that have the North pole of the magnetic strip and North pole if facing body, watches with the positive electrical field of the battery facing the body, and metal earrings, necklaces and bracelets. Carrying or wearing these items should be avoided while taking antibiotics, as should the electrical magnetic fields of computers, televisions, microwaves, and cellular telephones. If treatment appears to be ineffective, interference from the items listed above should be considered.

Within a few months after apparently successful antibiotic treatment, with disappearance of both the symptoms and the underlying infection, the *Chlamydia trachomatis* infection often reappeared together with localized Hg deposits and elevated Uric acid levels. Recurrences of the various infections often coincided with sudden seasonal changes in environmental temperature. Since *Chlamydia trachomatis* retreats from the originally infected area(s) to 3–5 highly specific, warm and moist locations, (i.e. the sublingual caruncle, the right and left axillae, the genitals, the maxillary, ethmoid & frontal sinuses and small part of nostrils, and the insulin-like Growth Factor positive horizontal lines above and below the knees), eliminating the *Chlamydia trachomatis* from these sites by enhancing drug uptake of the antibiotics specifically in these areas by stimulating their corresponding organ representation areas on the hands or other parts of the body, like the scalp, ears, and feet is desired. However, even when the antibiotics were successfully and continuously delivered, the *Chlamydia trachomatis* failed to yield to the treatment.

With *Chlamydia trachomatis* infections there is the co-existence of abnormal Hg deposits and abnormally elevated levels of Uric acid in the 5 localized areas mentioned above. Since Uric acid is produced by *Chlamydia trachomatis*, by removing the Hg allows effective antibiotics, delivered by drug uptake enhancement methods, to eliminate the infection which would then result in reduction of the Uric acid. Similarly in the Herpes Family Virus infections the inventor often found abnormal Hg deposits which should be eliminated in the same 5 localized areas.

Localized Hg deposits existing in all 5 of these areas were found to be contributing to the imperviousness of the microorganisms to the antibiotic. Removing Hg deposits from various parts of the body resulting from the decay of radioactive Thallium 201 injected for cardiac SPECT, can be by using Chinese parsley orally, rather than more drastic intravenous chelating agents which remove heavy metals but also take calcium and other essential substances from the body. Treatment of *Chlamydia trachomatis*, as well as Herpes Family Viral infections may be in the same manner, i.e. the combined use of antibiotics like Doxycycline for *Chlamydia trachomatis* or EPA/DHA as an antiviral agent for Herpes Family Viruses together with Chinese parsley to remove localized Hg deposits, and regular use of drug uptake enhancement methods to promote delivery of the substances to the infected areas and their uptake in these sites. The use of controlled dosages of Chinese parsley completely eliminates *Chlamydia trachomatis*, Herpes Simplex Viruses Types I and II, and Cytomegalovirus in 11 subjects. This inventor's study also indicated Chinese parsley also enhances urinary excretion of Ni and Cd, in addition to, Hg, Pb and Al.

Further clinical applications of this method appear beneficial in the treatment of other diseases which may involve localized deposits of metals, i.e. Hg, Pb, Ni, Cd and Al such as the following:

1. Cancer and Precancer (Viral infection and Hg)
2. Essential Hypertension (Viral or Bacterial infection and Hg and/or Pb)
3. Minamata Disease (Viral, Ricketial or Bacterial infection and Hg)
4. Amyotrophic Lateral Sclerosis (Viral infection and Hg)
5. Multiple Sclerosis (Multiple Mixed Viral, Bacterial, Ricketial infections and Hg and/or Pb)
6. Alzheimer's Disease (Multiple Mixed Viral, Bacterial and Ricketial infection and AL)
7 Chronic pain caused by Herpes Simplex Type I and/or Herpes Simplex II (Viral infection and Hg and/or Pb)
8. Rheumatoid Arthritis with *Chlamydia trachomatis* and/ or *Lyme Borrelia Burgorferi* infection in the painful joints (Mixed infections and Hg)
9. Lead and/or Mercury Poisoning (often with subclinical viral infection in the brain)
10. Itaita Disease (Viral or Bacterial infection and Cd)
11. Stroke (Viral infection and Pb with or without Hg)
12. Psoriasis (Viral infection and Hg with or without Hg)
13. Intractable Dental and Periodontal Infection (Various infection and Hg with or without Pb)

Many of the above diseases are found to be associated with various types of infections which co-exist with various metal deposit in the pathological areas, according to the Bi-Digital O-Ring Test.

Similar treatment to patients with various cancers and pre-cancerous conditions verified by biopsies appear encouraging. In cancer and pre-cancerous tissues there is co-existence of the following 5 parameters:

1) significant presence of Oncogene C-fos $Ab_2$
2) significant presence of Integrin $\alpha 5\beta 1$
3) significant presence of Hg deposits
4) Acetylcholine =0
5) significant presence of virus Simultaneous occurrence of all of the 5 conditions listed above allows for identification of cancer or pre-cancer, since each one individually may, or may not, have significance to cancer. As in the treatment for *Chlamydia trachomatis* and Herpes Family Viruses, it appears that the elimination of localized Hg deposits in body tissues allows therapeutic changes to occur in the co-existing conditions. If Hg can be eliminated by the Chinese parsley from cancer or precancer cells, and the virus can be inhibited by an effective antiviral substance, such as EPA 180 mg with DHA 120 mg, and Acetylcholine can be enhanced by improving microcirculation with the application of one of the drug uptake enhancement methods, the results that appear to occur are either the growth of the cancer cells is inhibited, or the cancer cells revert towards normaicy, and the remaining Integrin $\alpha_5\beta_1$ and Oncogene C-fos $Ab_2$ and cancer markers also gradually disappears. Therefore Chinese parsley tablets to reduce or eliminate Hg from the cancer cells, and the effective antiviral agent, EPA, 180 mg, with DHA, 120 mg, were given 4 times/day. Together with regular application of drug-uptake enhancement methods, these two dietary supplements have accomplished very promising results in the patients with various cancers treated so far. Examples are shown in the following three cancer cases.

Since, in all the cancers and precancer cells, the applicant's previous studies revealed the presence of mercury in the cancer cell nucleus and presence of virus, as a potential treatment of cancer, the mixture capsule of EPA 180 mg and DHA 120 mg as antiviral agent 4 times a day with drug uptake enhancment, and a Chinese parsley pill was given 3 times a day. In 3 patients, the size of the cancer significantly reduced in 3 male patients. One patient was about 71-years old, white male with prostate cancer and its metastasis to right inguinal area as well as sacral bone, with increased PSA (Prostate Specific Antigen) and CEA (Cancer Embryonic Antigen). The second patient was about 58-years old, white male musician with thyroid cancer which was metasized to the lung and thoracic vertebrae. The third patient was about 81-years old, white male who had cancer in the face (adenoide cystic carcinoma) which was surgically removed along with the left eye, and the cancer occurred 12 years later. All of these patients' cancers were markedly reduced in size with reduction of the cancer markers.

Thus by the present invention, its objects and advantages are realized and although a preferred embodiment has been disclosed and described in detail herein, its scope should not be limited thereby, rather its scope should be determined by that of the appended claims.

What is claimed is:

1. A method of treating resistant infections, cancer or other medical conditions with infection and coexisting localized deposits of metal in the pathological areas comprising the steps of:

diagnosing the particular condition of a patient by conventional medical techniques or the Bi-Digital O-Ring test method;

having the patient ingest either an appropriate antibiotic or antiviral agent; and having the patient also ingest a highly elevated concentration of greens taken from the Umbelliferae family of vegetables or an alcohol extract of an effective component of the Umbelliferae family with ethyl alcohol, over a sustained period of time, to remove the localized deposits of metals.

2. The method in accordance with claim 1 which further includes the step of:

subjecting the patient to drug uptake enhancement to increase the effectiveness of the antibiotic or antiviral agent and the concentrate of the greens.

3. The method in accordance with claim 2 wherein the drug uptake enhancement comprises one or more of the following steps:

Vigorous Shiatsu massage, vibration, or mechanical stimulation with a portable mechanical or electromechanical vibrator of organ representation areas on the hand or ears or feet for a period of at least 1–2 minutes 4 times per day or more frequently;

(+)Qi Gong energy stored paper placed directly on the organ representation areas for a minimum of at least 1–2 minutes 4 times per day or longer;

(+)Qi Gong energy stored paper placed on the cardiovascular representation area of the Medulla Oblongata on the occipital area of the scalp for a minimum of at least 1–2 minutes 4 times per day or kept continuously;

(+)Qi Gong energy stored paper placed on the affected areas on various parts of the body for a minimum of at least 1–2 minutes 4 times per day or kept continuously;

red light from tungsten bulb or preferably brighter Krypton bulb battery operated flashlight with red filter, or broad red spectra from a light emitting diode, or monochronal red laser light applied for a minimum of 1–2 minutes on the organ representation areas on the hand or ears or feet or directly on the pathological area at least 4 times per day or longer;

negative electrical field application to the organ representation areas or directly above pathological areas for a minimum of at least 1–2 minutes 4 times per day from a soft metal sheet connected to a series of 2–5 connected 9-volt batteries of a total of approximately 18–45 V or longer;

piezo electric pulse stimulation on the organ representation areas or directly above pathological areas, without creating pain, at least 4 times per day or more frequent applications;

south pole of magnetic field of approximately 800–3000 gauss applied for 1–2 minutes on the organ representation areas of the body at least 4 times per day; or acupuncture given 1–2 times per week to the appropriate point or area where there is no infection.

4. The method in accordance with claim 3 wherein the elevated concentration of greens homogenate after filtration is approximately 100 mg taken 3 or 4 times a day until the pathological condition is improved or eliminated, wherein the dried effective component following ethyl alcohol extract for one adult dose is usually less than 75 mg.

5. The method in accordance with claim 4 wherein the concentrate is made from the homogenate of the leaves of *coriandrum sativum*.

6. The method in accordance with claim 1 wherein the elevated concentration of greens of the Umbelliferae family of vegetables including cilantro and carrot greens, about 5–10 gm of fresh leaves for an average adult dose, by evaporating water, without removing any part of the homogenate, is, approximately, 0.5–1.0 gram, when most of the ineffective components are filtered, the effective part will be about 75 mg–125 mg; for an average adult 100 mg taken 3 or 4 times a day until the abnormal condition is improved or eliminated; effective components of the greens, for one adult dose can be completely extracted by 10–15% alcohol containing grape or plum wines of 20–40 cc approximately in one minute is as easy to drink as herb wines and can be taken 3 or 4 times per day; the ethyl alcohol extracted effective component in one adult dose is usually less than 75 mg; dried extract can be put into a capsule or formed by mechanical pressure into a tablet after mixing with a compatible non-interfering substance including some sugar base.

7. The method in accordance with claim 6 wherein the concentrate is made from leaves of *Coriandrum Sativum*.

8. The method in accordance with claim 7 wherein the antiviral agent is EPA with DHA.

9. The method in accordance with claim 8 wherein the EPA is approximately 180 mg and the DHA is approximately 120 mg.

10. The method in accordance with claim 1 wherein the antiviral agent is EPA with DHA.

11. The method in accordance with claim 10 wherein the EPA is approximately 180 mg and the DHA is approximately 120 mg for an average adult dose.

12. The method in accordance with claim 10 wherein the condition being treated comprises one or more of the following:

Cancer and Precancer Viral infection and Hg;

Essential Hypertension Viral or Bacterial infection and Hg and/or Pb;

Minamata Disease Viral, Ricketial or Bacterial infection and Hg;

Amyotrophic Lateral Sclerosis Viral infection and Hg;

Multiple Sclerosis Multiple Mixed Viral, Bacterial, Ricketial infections and Hg and/or Pb;

Alzheimer's Disease Multiple Mixed Viral, Bacterial and Ricketial infection and AL;

Chronic pain caused by Herpes Simplex Type I and/or Herpes Simplex II Viral infection and Hg and/or Pb;

Rheumatoid Arthritis with *Chlamydia trachomatis* and/or Lyme Borrelia Burgorferi infection in the painful joints Mixed infections and Hg;

Lead and/or Mercury Poisoning often with subclinical viral infection in the brain;

Itaita Disease Viral or Bacterial infection and Cd;

Stroke Viral infection and Pb with or without Hg;

Psoriasis Viral infection and Hg with or without Hg; and

Intractable Dental and Periodontal Infection Various infection and Hg with or without Pb.

13. The method in accordance with claim 10 wherein the metal being removed is one or more of the following: Hg, Pb, Ni, Cd or Al.

14. The method in accordance with claim 1 wherein the condition being treated comprises one or more of the following:

Cancer and Precancer Viral infection and Hg;

Essential Hypertension Viral or Bacterial infection and Hg and/or Pb;

Minamata Disease Viral, Ricketial or Bacterial infection and Hg;

Amyotrophic Lateral Sclerosis Viral infection and Hg;

Multiple Sclerosis Multiple Mixed Viral, Bacterial, Ricketial infections and Hg and/or Pb;

Alzheimer's Disease Multiple Mixed Viral, Bacterial and Ricketial infection and AL;

Chronic pain caused by Herpes Simplex Type I and/or Herpes Simplex II Viral infection and Hg and/or Pb;

Rheumatoid Arthritis with *Chlamydia trachomatis* and/or Lyme Borrelia Burgorferi infection in the painful joints Mixed infections and Hg;

Lead and/or Mercury Poisoning often with subclinical viral infection in the brain;

Itaita Disease Viral or Bacterial infection and Cd;

Stroke Viral infection and Pb with or without Hg;

Psoriasis Viral infection and Hg with or without Hg; and

Intractable Dental and Periodontal Infection Various infection and Hg with or without Pb.

15. The method in accordance with claim 1 wherein the metal being removed is one or more of the following: Hg, Pb, Ni, Cd or Al.

16. The method in accordance with claim 1 wherein the greens comprise the leaf of *Coriandrum Sativum* and the effective component includes Bergapten, Umbelliferone, Scopoletin, Xanthotoxol with or without imperatorin, Beta-sitosterol, and Alpha-Amyrin, individually or in combination with each other.

17. The method in accordance with claim 1 wherein the greens comprise carom petroselinum parsley and the effective component includes Apiin, Bergapten, Isoiperatorin, Apiol, Apiolin, Myristicin, individually or in combination with each other.

* * * * *